US008715621B2

(12) United States Patent  
Swager et al.

(10) Patent No.: US 8,715,621 B2  
(45) Date of Patent: May 6, 2014

(54) RADICAL POLARIZING AGENTS FOR DYNAMIC NUCLEAR POLARIZATION

(75) Inventors: Timothy Manning Swager, Newton, MA (US); Robert Guy Griffin, Newton, MA (US); Olesya Haze, Cambridge, MA (US); Bjorn Corzilius, Cambridge, MA (US); Albert A. Smith, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/421,789

(22) Filed: Mar. 15, 2012

(65) Prior Publication Data

US 2013/0243698 A1 Sep. 19, 2013

(51) Int. Cl.
*A61B 5/055* (2006.01)
*C07D 257/08* (2006.01)

(52) U.S. Cl.
USPC ........... 424/9.3; 424/9.33; 544/179; 544/183; 544/243

(58) Field of Classification Search
USPC .......... 424/9.3, 9.33; 514/183, 243, 310, 658; 544/179, 183
See application file for complete search history.

(56) References Cited

U.S. PATENT DOCUMENTS

| | | | |
|---|---|---|---|
| 4,521,732 A | 6/1985 | Pegg et al. | |
| 4,682,107 A | 7/1987 | Bendall et al. | |
| 5,085,748 A | 2/1992 | Yamasaki et al. | |
| 5,145,893 A | 9/1992 | Galbo et al. | |
| 5,435,991 A | 7/1995 | Golman et al. | |
| 6,278,893 B1 | 8/2001 | Ardenkjaer-Larson et al. | |
| 6,311,086 B1 | 10/2001 | Ardenkjaer-Larsen et al. | |
| 6,455,542 B1 | 9/2002 | Anggard et al. | |
| 6,515,260 B1 | 2/2003 | Anderson | |
| 7,102,354 B2 | 9/2006 | Ardenkjaer-Larsen et al. | |
| 7,351,402 B2 | 4/2008 | Griffin et al. | |
| 7,985,594 B2 | 7/2011 | Griffin et al. | |
| 2002/0029586 A1 | 3/2002 | Driehuys | |
| 2002/0058869 A1 | 5/2002 | Axelsson et al. | |
| 2002/0107439 A1 | 8/2002 | Hersman et al. | |
| 2004/0039281 A1 | 2/2004 | Cook et al. | |
| 2004/0049108 A1 | 3/2004 | Ardenkjaer-Larsen et al. | |
| 2005/0107696 A1 | 5/2005 | Griffin et al. | |
| 2009/0302842 A1 | 12/2009 | Griffin et al. | |
| 2009/0311189 A1 | 12/2009 | Griffin et al. | |

FOREIGN PATENT DOCUMENTS

| | | |
|---|---|---|
| WO | WO 96/39367 | 12/1996 |
| WO | WO 2007/134160 | 11/2007 |
| WO | WO 2008/048714 | 4/2008 |

OTHER PUBLICATIONS

Eric L. Dane et al. Synthesis of a Water-Soluble 1,3-bis(diphenylene)-2-phenylallyl(BDPA) Radical, J. Org. Chem, 75(10), 3533-3536, 2010.*
Haze, et al. Water-soluble narrow-line radicals for dynamic nuclear polarization, Journal of the American Chemical Society, 134:14287-14290 (2012).
Dane, et al., Synthesis of a water-soluble 1,3-bis(diphenylene)-2-phenylally1 radical, Journal of Organic Chemistry, 75:3533-3536 (2010).
Written Opinion for PCT/US2013/30595, 11 pages (Jul. 10, 2013).
International Search Report for PCT/US2013/30595, 5 pages (Jul. 10, 2013).
Afeworki et al., "Selective Observation of the Interface of Heterogeneous Polycarbonate/Polystyrene Blends by Dynamic Nuclear Polarization Carbon-13 NMR Spectroscopy", *Macromolecules*, 25: 4084-4091 (1992).
Afeworki et al., "Mechanisms of DNP-Enhanced Polarization Transfer across the Interface of Polycarbonate/Polystyrene Heterogeneous Blends", *Macromolecules*, 25: 4092-4096 (1992).
Afeworki et al., "Molecular Dynamics of Polycarbonate Chains at the Interface of Polycarbonate/Polystyrene Heterogeneous Blends", *Macromolecules*, 25: 4097-4099 (1992).
Afeworki et al., "Direct Electron-to-Carbon Polarization Transfer in Homogeneously Doped Polycarbonates", *Macromolecules*, 25: 4100-4105 (1992).
Ardenkjaer-Larsen et al., "Increase in signal-to-noise of >10,000 times in liquid-state NMR", *Proc. Natl. Acad. Sci. U.S.A.* 100(18): 10158-10163 (2003).
Bagryanskaya et al., "Dynamic and stimulated nuclear polarization in photochemical radical reactions", *Russian Chemical Reviews*, 69 (11): 925-945 (2000).
Bajaj et al., "Dynamic nuclear polarization at 9T using a novel 250 GHz gyrotron microwave source", *Journal of Magnetic Resonance*, 160: 85-90 (2003).
Bajaj et al. "Dynamic Nuclear Polarization for Sensitivity-Enhanced Solid State NMR of Bateriorhodopsin", *Biophysical Society 49th Annual Meeting* Feb. 12-16, 2005, 88, 203A-203A. (abstract only).
Becerra et al. "Dynamic Nuclear Polarization with a Cyclotron Resonance Maser at 5 T", *Physical Review Letters*, 71(21): 3561-3564 (1993).
Bosman et al., "Five Generations of Nitoxyl-Functionalized Dendrimers", *Macromolecules*, 30: 3606-3611 (1997).
Chachaty et al., "Dynamic Behaviour of a Nitroxide Biradical Undergoing Multiple Internal motions: an EDR and $^{13}$C NMR Relaxation Study", *Magnetic Resonance in Chemistry*, 33: S174-S177 (1995).
Farrar et al., "High-Frequency Dynamic Nuclear Polarization in the Nuclear Rotating Frame", *Journal of Magnetic Resonance*, 144:134-141 (2000).
Farrar et al., "Mechanism of dynamic nuclear polarization in high magnetic fields," *Journal of Chemical Physics*, 114(11): 4922-4933 (2001).
Ferguson et al., "Temperature-Jump MAS NMR with a Laser Heater", *Journal of Magnetic Resonance*, Series A 109: 273-275 (1994).
Ferguson et al. "Transient Methods for in Situ NMR of Reaction on Solid Catalysts Using Temperature Jumps", *Anal. Chem.*, 67: 3342-3348 (1995).

(Continued)

*Primary Examiner* — Michael G Hartley
*Assistant Examiner* — Jagadishwar Samala
(74) *Attorney, Agent, or Firm* — Choate, Hall & Stewart, LLP; Charles E. Lyon; Xiaodong Li

(57) ABSTRACT

The present invention provides a variety of radicals, which are useful as polarizing compounds. Exemplary radicals are represented by compounds of Structural Formulae (I), (II), (III) and (IV) as described herein.

32 Claims, 5 Drawing Sheets

(4 of 5 Drawing Sheet(s) Filed in Color)

(56) References Cited

OTHER PUBLICATIONS

Franks et al., "Magic-Angle Spinning Solid-State NMR Spectroscopy of the β1 Immunoglobulin Binding Doman of Protein G (GB1): $^{15}N$ and $^{13}C$ Chemical Shift Assignments and Conformational Analysis", *J. Am. Chem. Soc.*, 127: 12291-12305 (2005).

Gagnaire et al., "Regulation by Potassium Ions of Spin Exchange and Dipolar Splitting in Biradical. A Simple Allosteric System," *Tetrohedron Letters*, 30(47):6507-6510 (1989).

Gerfen et al., "High Frequency (140 GHz) dynamic nuclear polarization: Polarization transfer to a solute in frozen aqueous solution", *J. Chem. Phys.*, 102(24): 9494-9497 (1995).

Hall et al., "Polarization-Enhanced NMR Spectroscopy of Biomolecules in Frozen Solution", *Science*, 276: 930-932 (1997).

Henstra et al. "High Dynamic Nuclear Polarization at Room Temperature," *Chemical Physics Letters*, 165(1): 6-10 (1990).

Hu et al., "Dynamic Nuclear Polarization with Biradicals", *J. Am. Chem. Soc.*, 126: 10844-10845 (2004).

Hu et al. "High-frequency dynamic nuclear polarization using biradicals: A multifrequency EPR lineshape analysis", *The Journal of Chemical Physics*, 128: 052302-1-052302-17 (2008).

Igumenova et al., "Assignments of Carbon NMR Resonance for Microcrystalline Ubiquitin", *J. Am. Chem. Soc.*, 126: 6720-6727 (2004).

International Preliminary Report on Patentability for PCT/US2007/068654 (Publication No. WO 2007/134160) mailed Nov. 17, 2008.

International Preliminary Report on Patentability for PCT/US2007/068659 (Publication No. WO 2008/048714) mailed Nov. 17, 2008.

International Search Report for PCT/US2007/068654 (Publication No. WO 2007/134160) mailed Feb. 13, 2008.

International Search Report for PCT/US2007/068659 (Publication No. WO 2008/048714) mailed Jul. 7, 2008.

Kirste et al., "ESR and ENDOR Investigations of Spin Exchange in Mixed Galvinoxyl/Nitroxide Biradicals. Syntheses", *J. Am. Chem. Soc.*, 104:3850-3858 (1982).

Kopf et al. "Magnetic Resonance Studies of Polyradicals. 11.[1] Nitronyl Nitroxide Biradicals, Nitroxide Tri- and Tetraradicals", *J. Am. Chem. Soc.*, 92(15): 4531-4535 (1970).

Luckhurst et al., "Interpretation of Biradical Electron Resonance Spectra", *J. Am. Chem. Soc.*, 92(15): 4738-4739 (1970).

Luckhurst et al., "Biradical as Spin Probes" in Spin Labeling Theory and Applications, pp. 133-181, L. Berliner Editor, Academic Press (1976).

Mak et al., "Chromophore Torsion Early in the Bacteriorhodopsin Photocyle", *J. Biophys. J.* 2005, 88, 506A-506A. (abstract only).

Martin et al., "Determination of End-to-End Distances in a Series of TEMPO Diradicals of up to 2.8 nm Length with a New Four-Pulse Double Electron Electron Resonance Experiment", *Angewandte Chemie International Edition*, 37(20): 2834-2837 (1998).

Martin et al., "Preparation of protein nanocrystals and their characterization by solid state NMR", *Journal of Magnetic Resonance*, 165: 162-174 (2003).

Nelson et al., "Structure of the Cross-β spine of amyloid-like fibrils", *Nature*, 435:773-778 (2005).

Reddy et al., "General Synthesis of Persistent Trityl Radicals for EPR Imaging of Biological Systems", *J. Org. Chem.*, 67(14): 4635-4639 (2002).

Rosay et al., "Sensitivity-Enhanced NMR of Biological Solids: Dynamic Nuclear Polarization of Y21M fd Bacteriophage and Purple Membrane", *J. Am. Chem. Soc.*, 123: 1010-1011 (2001).

Rosay et al., "Two-Dimensional $13_C$-$13_C$ Spectroscopy with Magic Angle Spinning and Dynamic Nuclear Polarization," *J. Am. Chem. Soc.*, 124: 3214-3215 (2002).

Rosay et al., "High Frequency Dynamic Nuclear Polarization in MAS Spectra of Membrane and Soluble Proteins," *J. Am. Chem. Soc.*, 125:13626-13627 (2003).

Singel et al., "A Spectrometer for EPR, DNP, and Multinuclear High-Resolution NMR", *Journal of Magnetic Resonance*, 81:145-161 (1989).

Song et al., "TOTAPOL: A Biradical Polarizing Agent for Dynamic Nuclear Polarization Experiments in Aqueous Media", *J. Am. Chem. Soc.*, 128: 11385-11390 (2006).

Turro et al., "An Electron Spin Polarization Study of the Interaction of Photoexcited Triplet Molecules with Mono-and Polynitroxyl Stable Free Radicals," *J. Phys. Chem.*, 97: 1138-1146 (1993).

Van Den Heuvel et al "Transient oscillations in pulsed dynamic nuclear polarization," *Chemical Physics Letters*, 188(3,4): 194-200 (1992).

Van Der Wel et al., "Dynamic Nuclear Polarization of Amyloidogenic Peptide Nanocrystals: GNNQQNY, a Core Segment of the Yeast Prion Protein, Sup35p", *J. Am. Chem. Soc.*, 128: 10840-10846 (2006).

Vostrikova et al., "New Chelating Nitroxide Free Radical Ligands for Heterospin-Magnetic Engineering", *European Journal of Inorganic Chemistry*, pp: 1181-1187 (1999).

Written Opinion for PCT/US2007/068654 (Publication No. WO 2007/134160) mailed Feb. 13, 2008.

Written Opinion for PCT/US2007/068659 (Publication No. WO 2008/048714) mailed Jul. 7, 2008.

Bates, R.D., et al., "Dynamic Fluorine-19 Polarization in Fluorinated Strained Cyclic Alkanes and Alkenes," The Journal of Physical Chemistry, 80(30):320-323 (1976).

Bezvershenko, I.A., et al., "Synthesis of a Water-Soluable Verdazyl Radical," Chemistry Heterocyclic Compounds (1985), 21, 946.

Butkovic, V., et al., "Kinetic Study of Flavonoid Reactions with Stable Radicals," J. Agric. Food Chem., 52:2816-2820 (2004).

Dane, E.L., et al., "Synthesis of a Water-Soluable 1,3-bis(diphenylene)-2-phenylallyl (BDPA) Radical," J. Org. Chem., 75(10):3533-3536 (2010).

Gorini, L., et al., "Addressing single molecules of a thin magnetic film," Inorganica Chimica Acta, 361:4089-4093 (2008).

Ionita, P., et al., "Synthesis and Charactization of Some Novel Homo- and Hetero-Diradicals of Hydrazyl and Nitroxide Type," Aust. J. Chem., 60:173-179 (2007).

Ionita, G., et al., "A New Crown Compound with Multifunctional Capabilities," Journal of Inclusion Phenomena and Macrocyclic Chemistry, 45:79-82 (2003).

Lumata, L.L., et al., "DPPH as DNP Polarizing Agent: ESR Investigation at 94 GHz and 240 GHz," National High Magnetic Field Laboratory 2011 Research Report (1 page).

Rozantsev, C., "Organic Chemistry of Free Radicals," Chapter 6 (1979) (abstract).

Yordanov, N.D., et al., "DPPH as a Primary Standard for Quantitative EPR Spectrometry," Appl. Magn. Reson., 6:341-345 (1994).

Yordanov, N.D., et al., "Quantitative spectrophotometric and EPR-determination of 1,1-diphenyl-2-picryl-hydrazyl (DPPH)," Fresenius J. Anal. Chem., 358:610-613 (1997).

\* cited by examiner

RADICAL POLARIZING AGENTS FOR DYNAMIC NUCLEAR POLARIZATION

GOVERNMENT FUNDING

This invention was made with Government support under Grant Nos. R01 EB002804 and R01 GM095843 awarded by the National Institutes of Health. The Government has certain rights in this invention.

COLOR DRAWINGS

The patent or application file contains at least one drawing executed in color. Copies of this patent or patent application publication with color drawing(s) will be provided by the Office upon request and payment of the necessary fee.

BACKGROUND OF THE INVENTION

The last decade has witnessed a renaissance in the development of approaches to prepare samples with high nuclear spin polarizations with the goal of increasing signal intensities in nuclear magnetic resonance (NMR) spectra and magnetic resonance imaging (MRI) images. These approaches have included high frequency, microwave driven dynamic nuclear polarization (DNP), para hydrogen induced polarization (PHIP), polarization of noble gases such as He, Xe and more recently Kr, and optically pumped nuclear polarization of semiconductors and photosynthetic reaction centers and other proteins. Dynamic nuclear polarization is an approach in which the large spin polarization in an electron spin system is transferred to a nuclear spin reservoir via microwave irradiation of the electron paramagnetic resonance (EPR) spectrum. The electron spin system in DNP is provided by a endogenous or exogenous paramagnetic polarizing agent. Most current research in these areas is aimed at the study of biological systems in aqueous environment, therefore, water soluble free radical compounds are desired. Many stable radicals, however, have water solubilities that limit their usefulness in aqueous systems. Moreover, a recent attempt to produce a water-soluble radicals with suitable properties for DNP had limited success (Dane and Swager, *J. Org. Chem.* 75(10):3533-3536 (2010)).

SUMMARY OF THE INVENTION

In one aspect, the present invention provides compounds represented by one of Structural Formulae (I)-(IV):

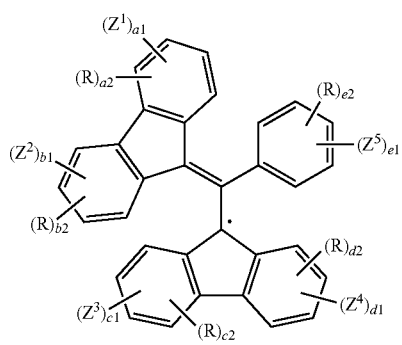

(I)

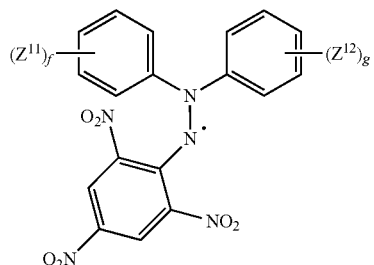

(II)

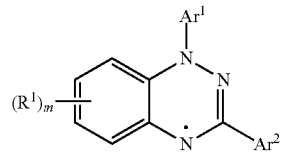

(III)

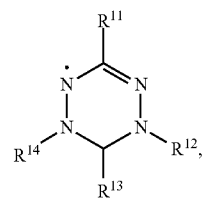

(IV)

wherein:

each R is independently —R', —OR', —SR', halogen, —CN, —NO$_2$, —NR'R", polyethyleneglycol, —COOR', —OCOR', —CONR'R", or NR'COR" or two R on adjacent carbon atoms taken together are

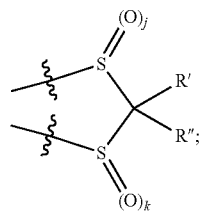

each $R^1$ is independently $Z^{21}$, halogen, —CN, —NO$_2$, an optionally substituted alkyl or an optionally substituted alkoxy;

$Ar^1$ and $Ar^2$ are independently optionally substituted aryl or heteroaryl, wherein at least one of $Ar^1$ and $Ar^2$ is substituted by at least one $Z^{22}$;

$R^{11}$, $R^{12}$ and $R^{14}$ are independently —H, optionally substituted alkyl or optionally substituted aryl;

$R^{13}$ is =H, =O, =S, optionally substituted alkyl or optionally substituted aryl, wherein at least one of $R^{11}$, $R^{12}$, $R^{13}$ and $R^{14}$ is substituted with at least one $Z^{31}$;

R' and R" are independently —H, an optionally substituted alkyl or an optionally substituted aryl;

$Z^1$-$Z^5$, $Z^{11}$-$Z^{12}$, $Z^{21}$-$Z^{22}$ and $Z^{31}$ are each independently —SO$_2$X, —SO$_3$X or —SO$_2$NR'R";

X is a cation;

a1, b1, c1 and d1 are each integers from 0 to 4, wherein the sum of a1, b1, c1 and d1 is one or greater;

a2, b2, c2 and d2 are each independently integers from 0 to 4;

e1 and e2 are each independently an integer from 0 to 5;

f and g are each integers from 0 to 4, where the sum or f and g is two or three or greater;

j and k are independently integers from 0 to 2; and m is an integer from 0 to 4.

The invention also includes inter alia compositions and pharmaceutical compositions containing these compounds, along with methods for polarizing an unpaired electron spin and performing dynamic nuclear polarization using these compounds. In addition, the invention provides methods of increasing the nuclear magnetic resonance signal of sample and preparing a subject for magnetic resonance imaging using these compounds. In these compositions and methods, the compounds of the inventions can either be used alone or in combination with an additional stable radical.

DETAILED DESCRIPTION OF CERTAIN EMBODIMENTS OF THE INVENTION

Definitions

Figure 1:
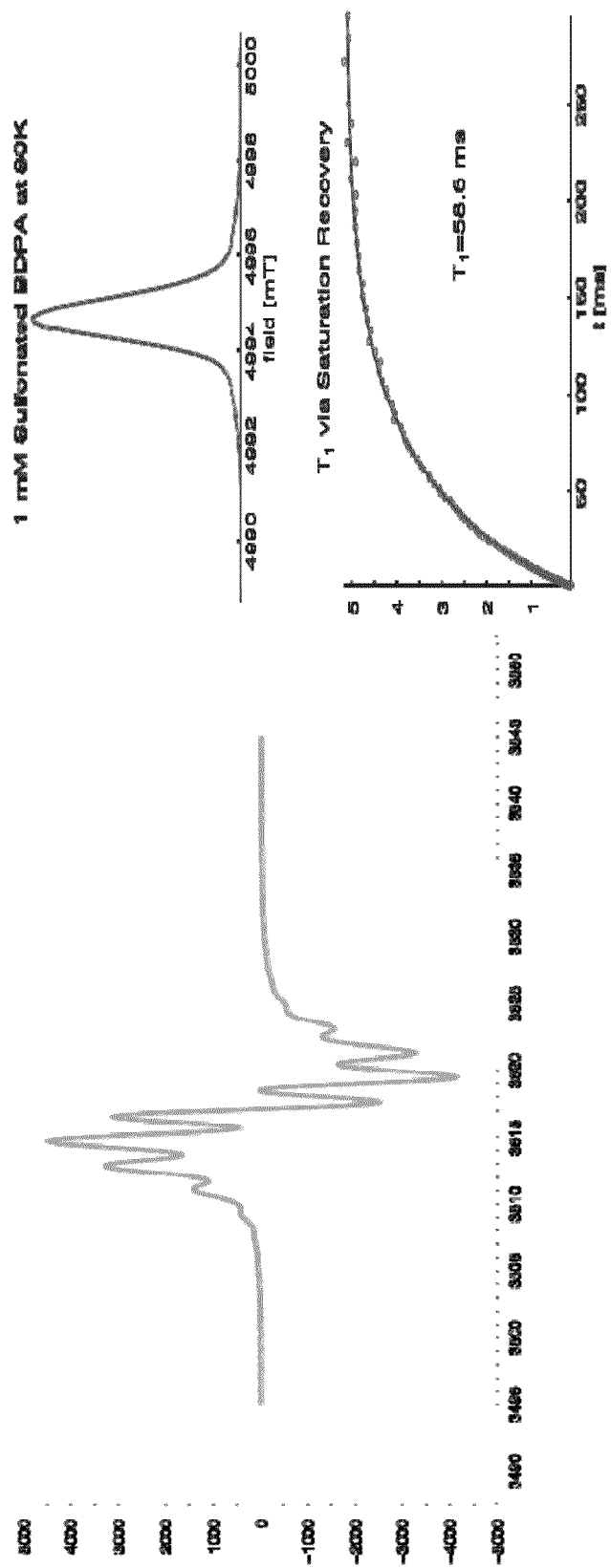
FIG. 1 shows the EPR spectrum of sulfonated BDPA made in Example 1 (SA-BDPA) at (A) 9.4 GHz EPR, room temperature, water; and (B) 140 GHz EPR, 84 K, $\Delta$=28 MHz.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

It will be appreciated that the inventive compound as described herein may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds.

The term "acyl," as used herein, refers to a group having the general formula —C(=O)R$^\circ$, where R$^\circ$ is substituted or unsubstituted hydroxyl, substituted or unsubstituted thiol, substituted or unsubstituted amino, substituted or unsubstituted, cyclic or acyclic aliphatic, substituted or unsubstituted, cyclic or acyclic heteroaliphatic, substituted or unsubstituted aryl, or substituted or unsubstituted heteroaryl. Exemplary acyl groups include carboxylic acids (—CO$_2$H), ketones (such as an acetyl group [—(C=O)CH$_3$], esters, amides, carbonates, carbamates, and ureas. Acyl substituents include, but are not limited to, any of the substituents described herein, that result in the formation of a stable moiety (for example, an aliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "aliphatic," as used herein, includes both saturated and unsaturated, nonaromatic, straight chain (i.e., unbranched), branched, acyclic, cyclic (i.e., carbocyclic), or polycyclic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-6 carbon atoms, or 2-6 carbon atoms. In certain embodiments, an aliphatic group has 1-5 or 2-5 carbon atoms. In certain embodiments, an aliphatic group has 1-4 or 2-4 carbon atoms. In certain embodiments, an aliphatic group has 1-3 or 2-3 carbon atoms. In certain embodiments, an aliphatic group has 1-2 carbon atoms. In certain embodiments, an aliphatic group has 1 carbon atom. In certain embodiments, an aliphatic group has 2 carbon atoms. Aliphatic group substituents include, but are not limited to, any of the substituents described herein, that result in the formation of a stable moiety (for example, an aliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, phosphino, cyano, amino, azido, nitro, hydroxy, thio, and/or halo groups).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-6 carbon atoms. In another embodiment, the alkyl group employed contains 1-5 carbon atoms. In still other embodiments, the alkyl group contains 1-4 carbon atoms. In yet another embodiments, the alkyl group contains 1-3 carbons. In yet other embodiments, the alkyl group contains 1-2 carbons. In yet other embodiments, the alkyl group contains 1 carbon atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like, which may bear one or more sustitutents. Alkyl group substituents include, but are not limited to, any of the substituents described herein, that result in the formation of a stable moiety (for example, an alkyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-6 carbon atoms. In some embodiments, the alkenyl group employed in the invention contains 2-5 carbon atoms. In another embodiment, the alkenyl group employed contains 2-4 carbon atoms. In still other embodiments, the alkenyl group contains 2-3 carbon atoms. In yet another embodiments, the alkenyl group contains 2 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (for example, an alkenyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-6 carbon atoms. In some embodiments, the alkynyl group employed in the invention contains 2-5 carbon atoms. In another embodiment, the alkynyl group employed contains 2-4 carbon atoms. In still other embodiments, the alkynyl group contains 2-3 carbon atoms. In still other embodiments, the alkynyl group contains 2 carbon atoms. Representative alkynyl groups include, but are not limited to, ethynyl, 2-propynyl(propargyl), 1-propynyl, and the like, which may bear one or more substituents. Alkynyl group substituents include, but are not limited to, any of the substituents described herein, that result in the formation of a stable moiety (for example, an alkynyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "amino," as used herein, refers to a group of the formula ($-NH_2$). A "substituted amino" refers to a group of the formulae ($-NHR^h$) or ($-NR^h_2$), wherein $R^h$ can be any substitutent except hydrogen which result in the formation of a stable moiety (for example, an amino group substituted with one or more aliphatic, alkyl, alkenyl, alkynyl, heteroaliphatic, heterocyclic, aryl, heteroaryl, acyl, sulfinyl, sulfonyl, amino, nitro, hydroxy, and/or thio groups). A "suitable amino-protecting group," as used herein, is well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (for example, an aryl group substituted with one or more aliphatic, heteroaliphatic, heterocyclic, aryl, heteroaryl; acyl, sulfinyl, sulfonyl, oxo, imino, thiooxo, cyano, amino, azido, nitro, hydroxy, thio, and/or halo groups).

The term "azido," as used herein, refers to a group of the formula (—$N_3$).

The term "cyano," as used herein, refers to a group of the formula (—CN).

The term "direct bond" or "bond" refers to a single, double or triple bond between two groups. In certain embodiments, a "direct bond" refers to a single bond between two groups.

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. As will be appreciated by one of ordinary skill in the art, "heteroaliphatic" is intended herein to include, but is not limited to, heteroalkyl, heteroalkenyl, heteroalkynyl, and heterocyclyl moieties. Thus, as used herein, the term "heteroalkyl" includes straight, branched and cyclic alkyl groups, as defined herein, which are optionally substituted with one or more functional groups, and that contain one or more oxygen, sulfur, nitrogen, phosphorus, or silicon atoms, e.g., in place of carbon atoms. An analogous convention applies to other generic terms such as "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-6 carbon atoms, or 2-6 carbon atoms. In certain embodiments, a heteroaliphatic group has 1-5 or 2-5 carbon atoms. In certain embodiments, a heteroaliphatic group has 1-4 or 2-4 carbon atoms. In certain embodiments, a heteroaliphatic group has 1-3 or 2-3 carbon atoms. In certain embodiments, a heteroaliphatic group has 1-2 carbon atoms. In certain embodiments, an heteroaliphatic group has 1 carbon atom. In certain embodiments, a heteroaliphatic group has 2 carbon atoms. Heteroaliphatic group substituents include, but are not limited to, any of the substituents described herein, that result in the formation of a stable moiety (for example, a heteroaliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, phosphino, cyano, amino, azido, nitro, hydroxy, thio, and/or halo groups).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (for example, a heteroaryl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "heterocyclic," or "heterocyclyl," as used herein, refers to an non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (for example, a heterocyclic group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "hydrogen," as used herein, refers to any isotope having an atomic number of 1. Typically, hydrogen refers to stable isotopes containing either zero or one neutrons (i.e., $^1$H or $^2$H, also known as deuterium). In certain embodiments, hydrogen is present in its normal isotopic abundance. In other embodiments, at least one position is specifically selected to have a deuterium present.

The term "hydroxy," or "hydroxyl," as used herein, refers to a group of the formula (—OH). A "substituted hydroxyl" refers to a group of the formula (—OR$^i$), wherein R$^i$ can be any substituent except hydrogen which results in a stable moiety (for example, a hydroxy group substituted with a suitable hydroxyl protecting group, an aliphatic, alkyl, alkenyl, alkynyl, heteroaliphatic, heterocyclic, aryl, heteroaryl, acyl, sulfinyl, and/or sulfonyl group). A "suitable hydroxyl protecting group" as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy) methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4'-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

The term "imino," as used herein, refers to a group of the formula (=NR'), wherein R' corresponds to hydrogen or any substitutent as described herein, that results in the formation of a stable moiety (for example, a suitable amino protecting group; substituted or unsubstituted amino; acyl; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; or substituted or unsubstituted heteroaryl).

The term "isocyano," as used herein, refers to a group of the formula (—NC).

The term "nitro," as used herein, refers to a group of the formula (—NO$_2$).

The term "nitroxide," as used herein, refers to a stable nitroxide group which may be cyclic or acyclic. In certain embodiments, a stable nitroxide refers to a chemically stable nitroxide which may be obtained in pure form, stored, and handled in the laboratory. In certain embodiments, a stable nitroxide refers to a cyclic or acyclic nitroxide which contains two groups which do not contain alpha hydrogens. Exemplary cyclic or acyclic nitroxides are provided in Keana, *Chemical Reviews* (1978) 78:37-64, the entirety of which is incorporated herein by reference.

The term "oxo," as used herein, refers to a group of the formula (=O).

The term "stable moiety," as used herein, preferably refers to a moiety which possess stability sufficient to allow manufacture (including manufacture in situ), and which maintains its integrity for a sufficient period of time to be useful for the purposes detailed herein.

The term "stable radical," as used herein, refers to a free radical that possesses stability sufficient to allow manufacture (including manufacture in situ), and which maintains its integrity for a sufficient period of time to be useful for the purposes detailed herein.

The term "thio," or "thiol," as used herein, refers to a group of the formula (—SH). A "substituted thiol" refers to a group of the formula (—SR'), wherein R' is any substitutent, except hydrogen, which results in the formation of a stable moiety (for example, a thio group substituted with one or more aliphatic, alkyl, alkenyl, alkynyl, heteroaliphatic, heterocyclic, aryl, heteroaryl, acyl, sulfinyl, and/or sulfonyl).

The term "thiooxo," as used herein, refers to a group of the formula (=S).

The term "subject," as used herein, include eukaryotes, such as mammals, e.g., humans, ovines, bovines, equines, porcines, canines, felines, non-human primates, mice, and rats.

The term "sulfinyl," as used herein, refers to a group of the formula $R^f$—S(=O)— wherein $R^f$ may be an optionally substituted aliphatic, heteroaliphatic, aryl, or heteroaryl. The term "alkyl sulfinyl" refers to a sulfinyl group where $R^f$ may be an optionally substituted alkyl group. The term "aryl sulfinyl" refers to a sulfinyl group where $R^f$ may be an optionally substituted aryl or heteroaryl group.

The term "sulfonyl," as used herein, refers the group of the formula $R^g$—S(=O)$_2$—, wherein $R^g$ may be an optionally substituted aliphatic, heteroaliphatic, aryl, or heteroaryl. The term "alkyl sulfonyl" refers to a sulfonyl group where $R^g$ may be an optionally substituted alkyl group. The term "aryl sulfonyl" refers to a sulfonyl group where $R^g$ may be an optionally substituted aryl or heteroaryl. Exemplary aryl or alkyl sulfonyl groups include tosyl (toluene sulfonyl, $CH_3C_6H_4SO_2$—), mesyl (methyl sulfonyl, $CH_3SO_2$—), and trifluoromethanesulfonyl ($CF_3SO_2$—).

Compounds

Compounds of the invention can be represented by Structural Formulae (I)-(IV):

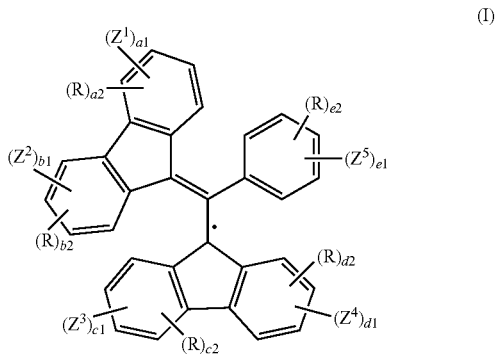

(I)

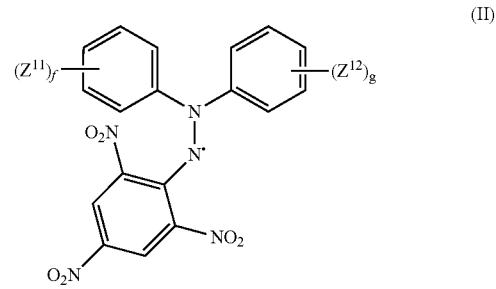

(II)

-continued

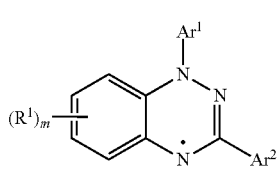
(III)

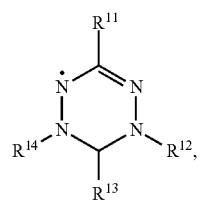
(IV)

wherein:
each R is independently —R', —OR', —SR', halogen, —CN, —NO$_2$, —NR'R", polyethyleneglycol, —COOR', —OCOR', —CONR'R", or —NR'COR", or two R on adjacent carbon atoms taken together are

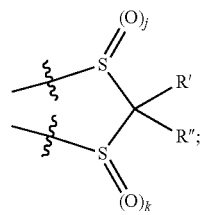

each $R^1$ is independently $Z^{21}$, halogen, —CN, —NO$_2$, an optionally substituted alkyl or an optionally substituted alkoxy;

$Ar^1$ and $Ar^2$ are independently optionally substituted aryl or heteroaryl, wherein at least one of $Ar^1$ and $Ar^2$ is substituted by at least one $Z^{22}$;

$R^{11}$, $R^{12}$ and $R^{14}$ are independently —H, optionally substituted alkyl or optionally substituted aryl;

$R^{13}$ is —H, =O, =S, optionally substituted alkyl or optionally substituted aryl, wherein at least one of $R^{11}$, $R^{12}$, $R^{13}$ and $R^{14}$ is substituted with at least one $Z^{31}$;

R' and R" are independently —H, an optionally substituted alkyl or an optionally substituted aryl;

$Z^1$-$Z^5$, $Z^{11}$-$Z^{12}$, $Z^{21}$-$Z^{22}$ and $Z^{31}$ are each independently —SO$_2$X, —SO$_3$X or —SO$_2$NR'R";

X is a cation;

a1, b1, c1 and d1 are each integers from 0 to 4, wherein the sum of a1, b1, c1 and d1 is one or greater;

a2, b2, c2 and d2 are each independently integers from 0 to 4;

e1 and e2 are each independently an integer from 0 to 5;

f and g are each integers from 0 to 4, where the sum or f and g is three or greater; and m is an integer from 0 to 4.

In certain embodiments, $Z^1$-$Z^5$, $Z^{11}$-$Z^{12}$, $Z^{21}$-$Z^{22}$ and $Z^{31}$ are each independently —SO$_3$X.

In certain embodiments, X is H$^+$, NR'R"R'"R"", Ag$^+$, Ca$^{2+}$, Ba$^{2+}$, Li$^+$, Na$^+$ or K$^+$ or a combination thereof and wherein R'" and R"" are each independently —H, an optionally substituted alkyl or an optionally substituted aryl. Both Ca$^{2+}$ and Ba$^{2+}$ can be present as either divalent cations or as (Ca(OH))$^+$ or (Ba(OH))$^+$. Typical values of X are Na$^+$ and K$^+$.

In certain embodiments, the compound is represented by Structural Formula (I):

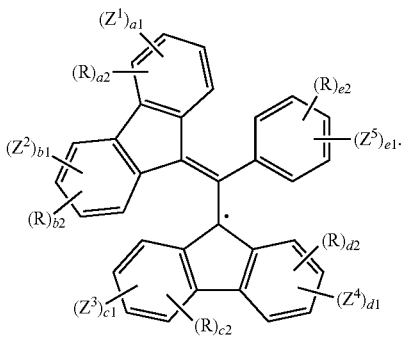
(I)

In particular embodiments, the values of a1-e1 and a2-e2 and the positions of R and $Z^1$—$R^5$ can be chosen to create a symmetrical molecule or an asymmetrical molecule. For these embodiments, typical values of R include $^1$H, $^2$H, halogen (e.g., bromo) and COOR' and typical values of $Z^1$-$Z^5$ include —SO$_3$X and —SO$_2$NR'R". These typical values of R and $Z^1$-$Z^5$ can be present either separately or in combination.

One group of compounds of Structural Formula (I) is represented by Structural Formula (Ia):

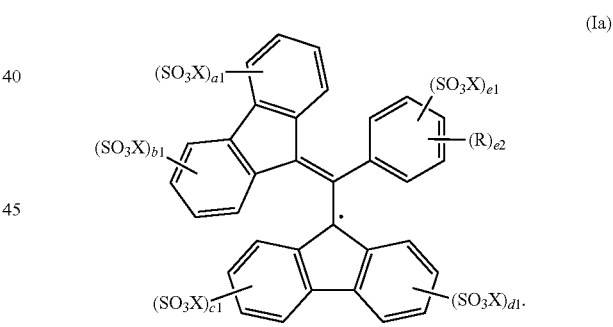
(Ia)

In certain embodiments, the sum of a1, b1, c1, d1 and e1 is from 2 to 7, such as from 2 to 5 or from 4 to 7, particularly 4 to 5. In particular embodiments, e2 is 0 or 1.

In certain embodiments, e1 is 1. For example, e1 can be 1 when e2 is 0 or 1.

In certain embodiments, e2 is 1. For example, e2 can be 1 when e2 is 0.

In certain embodiments, R is —COOR' (e.g., R' is H, methyl, ethyl) or a halogen (e.g., bromo). In other embodiments, R is a fluoroalkyl group, such as a $C_6$-$C_{16}$ or $C_8$-$C_{12}$ fluoroalkyl group. The fluoroalkyl group is optionally perfluorinated. In one example, R has one of these values when e1 is 0.

Examples of compounds of Structural Formula (I) include:

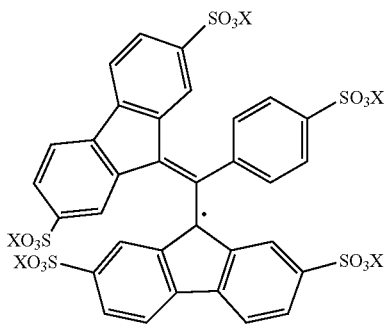

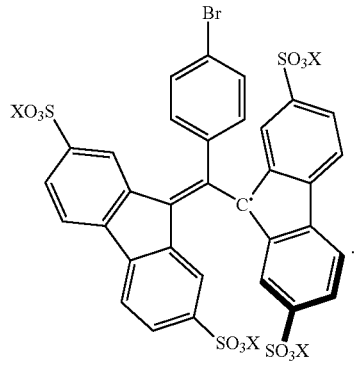

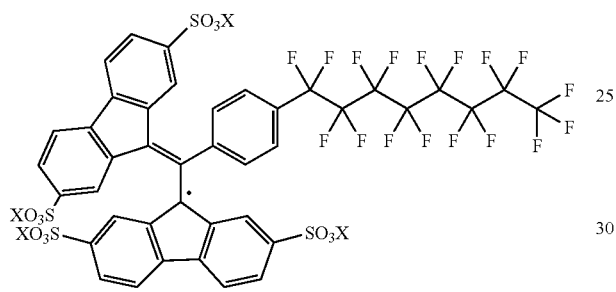

In certain embodiments, the compound is represented by Structural Formula (II):

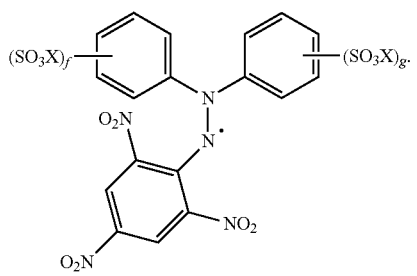

(II)

In exemplary embodiments, the sum of f and g is 3 or 4. For methods of the invention, the compound can also have the sum of f and g be 2, such as for the following compound:

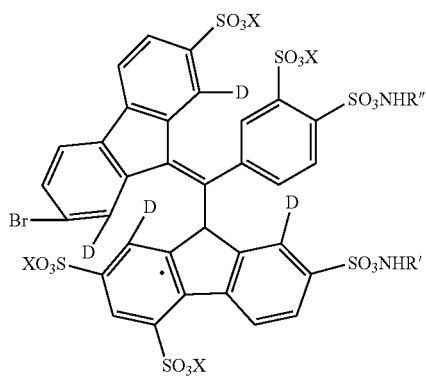

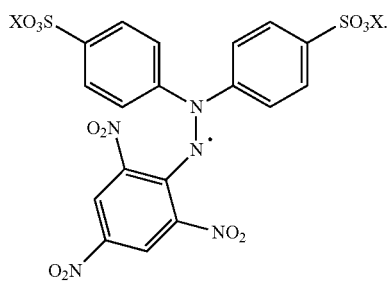

The invention also includes compounds represented by Structural Formula (III):

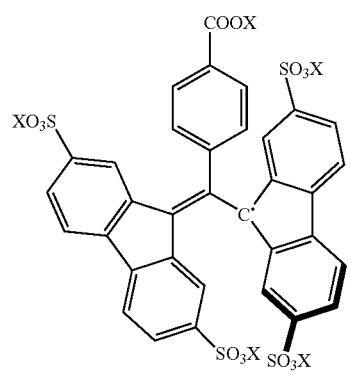

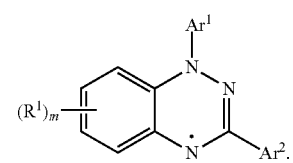

In certain embodiments, either or both of $Ar^1$ and $Ar^2$ are optionally substituted aryl, such as when either or both of $Ar^1$ and $Ar^2$ are optionally substituted phenyl. Typically, both $Ar^1$ and $Ar^2$ are optionally substituted phenyl.

One group of compounds of Structural Formula (III) are represented by Structural Formula (IIIa):

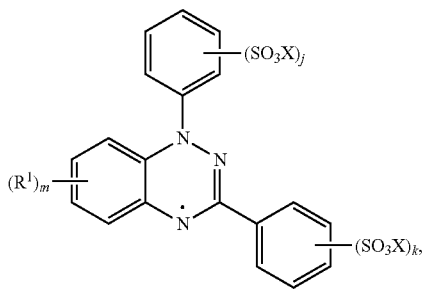

(IIIa)

where j and k are integers from 0 to 5 and the sum of j and k is at least one. For example, the sum of j and k can be two or three.

Particular compounds of Structural Formula (IIIa) are represented by Structural Formula (IIIb):

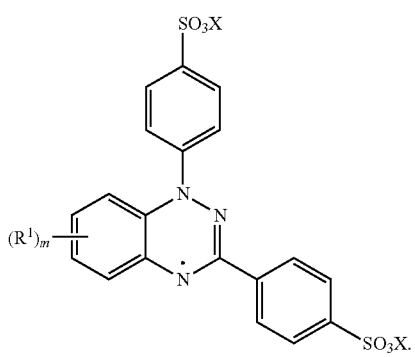

(IIIb)

In certain embodiments, m is 0. In other embodiments, $R^1$ is $Z^{21}$, methyl, ethyl, chloro, bromo or methoxy, such as when m is 1 or 2, typically 1. When present, $Z^{21}$ is typically —$SO_3X$.

The invention also includes compounds represented by Structural Formula (IV):

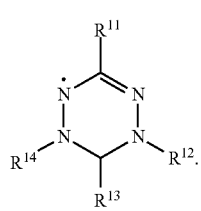

(IV)

In certain embodiments, $R^{11}$, $R^{12}$ and $R^{14}$ are each aryl. One group of compounds of Structural Formula (IV) is represented by Structural Formula (IVa):

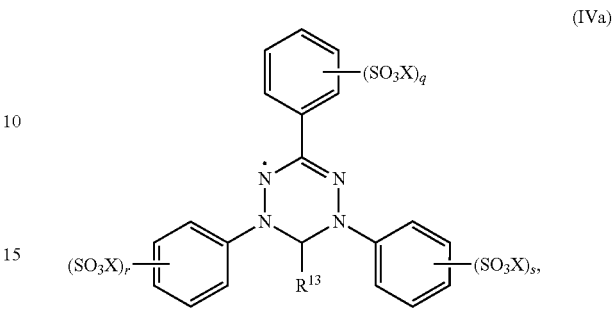

(IVa)

where q, r and s are each integers from 0 to 5, and the sum of q, r and s is at least 1. Typically, the sum of q, r and s is from 2 to 5, namely 2, 3, 4 or 5.

A particular group of compounds of Structural Formula (IVa) are represented by Structural Formula (IVb):

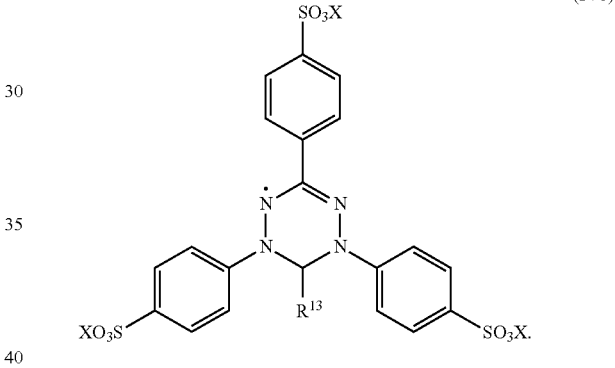

(IVb)

$R^{13}$ is typically —H or an optionally substituted alkyl, especially an unsubstituted $C_1$-$C_4$ alkyl. In certain embodiments, $R^{13}$ is —H.

In certain embodiments, one or more (or all) of the hydrogen atoms present in a compound of Structural Formula (I)-(IV), including those specifically shown above, are $^2H$.

Compositions

The compounds of the present invention can be present in a composition or a pharmaceutical composition. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Compositions may include one of the compounds described herein in combination with another stable radical. Examples of stable radicals include compounds containing 1,3-bisdiphenylene-2-phenylallyl (BDPA), nitroxides such as (2,2,6,6-Tetramethylpiperidin-1-yl)oxyl (TEMPO), hydrazyls as a diphenylpicrylhydradine (DPPH), and trityl moieties. In such compounds, a compound of the invention may be optionally associated with the other stable radical via electrostatic, hydrophobic or fluorous interactions. A particularly suitable combination contains a compound of Structural Formula (I) containing 2 to 7 (e.g., 4 to 5) —$SO_3X$ moieties, such as

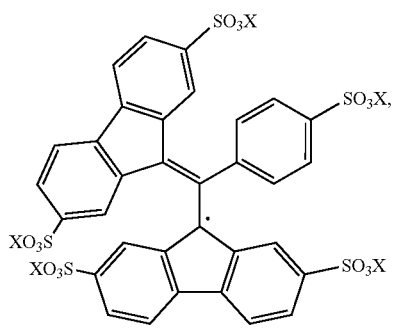

in mixture with TEMPO.

Certain compositions of the invention are present are micelles. For some micelles, a composition of the invention is mixed with a nonpolar radical, particularly a radical containing a perfluorinated moiety. The composition typically also includes a surfactant. One type of a perfluorinated radical is a TEMPO group with a fluorinated tail, preferably a perfluorinated tail (described in Pozzi, *Adv. Synth. Cat.* 347:677 (2005), the contents of which are incorporated by reference). An exemplary perfluorinated radical is TEMPO attached to a $C_6$-$C_{20}$ (such as $C_8$-$C_{12}$) perfluoroalkyl group via an amide or sulfonamide group at the 4-position of TEMPO. Suitable surfactants include perfluorinated sulfonic carboxylic acids, particularly $C_4$-$C_{12}$ acids such as $C_6$, $C_7$, $C_8$, $C_9$, $C_{10}$, $C_{11}$ and $C_{12}$ acids. Exemplary surfactants include ammonium perfluorooctanoate (FC143), perfluorooctanesulfonic acid (PFOS) and perfluorononanoic acid (PFNA).

Uses

Dynamic nuclear polarization (DNP) allows for increased sensitivity, due to increasing the nuclear magnetic resonance signal of a sample, and decreased measurement time. In addition, DNP allows observation of transient processes (e.g., protein folding, catalysis, and metabolic processes). DNP coupled with magic angle spinning solid state NMR (MAS-SSNMR) is very useful in the study of proteins which can not be crystallized, and therefore can not be studied by x-ray crystallography, e.g., transmembrane proteins. Also, the structure of insoluble amyloid fibrils have been elucidated recently with the help of DNP.

DNP increases the sensitivity of NMR through hyperpolarization of nuclear spins. Free radicals added to the NMR sample (or bound to the analyte) are the source of unpaired electron spins which are efficiently polarized in a magnetic field due to their high magnetic moment. Microwave irradiation of the sample transfers the large polarization of the unpaired electrons to the nuclei. Several polarization transfer mechanisms have been described. The Overhauser effect (OE) stems from the dipolar relaxation between electrons and nuclei, and allows for DNP in liquid solutions, but is not effective at fields higher than 1 T. The solid effect (SE) is operative when the paramagnetic centers are localized and the nuclear spin is coupled to one electron spin. To take advantage of SE a polarization agent with both the homogeneous EPR linewidth ($\delta$) and the inhomogeneous spectral breadth ($\Delta$) that are smaller than the nuclear Larmor frequency ($\delta$, $\Delta < \omega_{0I}$) is required. The cross effect (CE) is dominant in a three spin system (a biradical and nucleus with non-zero spin). The inhomogeneous breadth of the biradical EPR spectrum must be larger than the nuclear Larmor frequency, while homogeneous width must remain small. Finally, thermal mixing (TM) involves a homogeneously broad EPR line (larger than the nuclear Larmor frequency) from multiple dipolar coupled electrons. This condition requires high concentrations of paramagnetic polarizing agent.

A variety of DNP methods (e.g. Magic Angle Spinning (MAS) DNP, Dissolution DNP, Shuttle DNP) has been developed using different experimental conditions to take advantage of the different DNP mechanisms described earlier, however, a stable polarizing agent is a universal requirement.

Polarizing agents are the source of the unpaired electrons in the DNP experiments. The structure of the polarizing agent has a direct effect on the enhancement of the NMR signal via DNP. Because biological systems require aqueous environment, high water solubility is essential in the development of new polarizing agents. Narrow EPR linewidth ($\leq 40$ MHz at 211 MHz $^1$H Larmor frequency) is required for SE experiments as mentioned above, and biradicals with EPR resonances combining narrow homogeneous linewidth with inhomogeneous breadth matching the nuclear Larmor frequency will give the largest enhancements via CE.

The sensitivity in solid-state NMR (ssNMR) experiments can be enhanced by two to three orders of magnitude by dynamically polarizing the nuclear spin system prior to recording the NMR spectrum. This enhancement can be transferred into the liquid-state (e.g., liquid-state NMR or MRI) by melting the solid sample after polarization (e.g., as described herein and in US 2009/0311189), the contents of which are incorporated herein by reference). For MRI applications, at least a portion of the molten sample that includes a polarized analyte is administered into the subject being imaged prior to imaging.

The DNP procedure involves microwave irradiation of the electron paramagnetic resonance (EPR) spectrum of either an endogenous or exogenous paramagnetic species present in a sample, and results in the transfer of the greater spin polarization of the electrons to the nuclei of surrounding molecules. While the methods described herein are not limited to any specific magnetic field and the DNP procedure could be performed at low magnetic fields, the performance of DNP experiments at the high magnetic fields used in contemporary NMR experiments (e.g., 5-20 T) is affected by the following three factors.

First, a high frequency (140-600 GHz), high power (~10 watts) microwave source is typically used to drive the continuous-wave (CW) DNP transitions associated with the second order electron-nuclear dipolar interactions. To date this has been achieved by utilizing gyrotrons, because they operate in the requisite frequency range and produce suitable microwave powers.

Second, the relaxation times of the spin systems in the experiment dictate that it be optimally performed at low temperatures (usually ≤90 K). When obtaining high resolution ssNMR spectra of solids, magic-angle spinning (MAS) is preferably incorporated into the experiment. Thus, multiple resonance—i.e., $^1$H, $^{13}$C, $^{15}$N and e$^-$—low temperature MAS probes may be required for optimal execution of certain DNP experiments.

The third factor is the nature of the paramagnetic polarizing agent. Preferably, the polarizing agent should: (a) be compatible with the polarization mechanism that yields the optimal signal enhancement, namely the three-spin thermal mixing (TM) or cross effect (CE), (b) be useful in polarizing a large array of analytes ranging from small molecules to proteins, (c) produce large signal enhancements at a reduced concentration of paramagnetic species, and (d) be soluble in aqueous media. As noted above, we have previously described the use of a biradical that satisfies the first three of these criteria and yields improved DNP enhancements.

The present invention provides polarizing agents that satisfy the first three criteria as well as the fourth requirement (i.e., solubility in aqueous media). This last criterion is significant since it opens up a vast number of DNP-NMR and DNP-MRI applications that rely on aqueous media.

Similarly, in magnetic resonance imaging (MRI), polarization agents are useful. The contrast in MRI comes from three sources: the proton density of the tissue, and the spin lattice and spin-spin relaxation times, T1 and T2, of the tissue. The Ti describes the recovery of longitudinal magnetization, while T2, measured the loss of phase coherence in the transverse plane. The emphasis on each of these sources of contrast determines the image quality. Contrast agents, such Gd3+ complexes, decrease T1 and T2 of the tissue in their local environment, and therefore allow for greater contrast. However, there has been concern about the possible toxicity of gadolinium complexes in patients with renal insufficiency. Free gadolinium (Gd3+) is known to be toxic and must be tightly complexed by a ligand to be used in humans. The compounds described herein will increase contrast in MRI in a fundamentally different way than the contrast agents currently used in the clinic. The compounds of the invention rely on exogenously dynamically polarized nuclei with long T1s. Instead of monitoring differences in relaxation times, these materials will result in larger initial polarizations and therefore enhanced signal intensities and signal to noise.

The compounds of the present invention are also useful in measuring tissue oxygenation levels and pH via using spin-label EPR. Also, the compounds can be used in Overhauser magnetometers, along with superconducting quantum interference devices (SQUIDs).

In certain embodiments, the methods involve (a) providing a frozen sample in a magnetic field, wherein the frozen sample includes a compound described herein and an analyte with at least one spin half nucleus; (b) polarizing the at least one spin half nucleus of the analyte by irradiating the frozen sample with radiation having a frequency that excites electron spin transitions in the compound; (c) optionally melting the sample to produce a molten sample; and (d) detecting nuclear spin transitions in the at least one spin half nucleus of the analyte in the frozen or molten sample. In certain embodiments, the methods further comprise a step of freezing a sample in a magnetic field to provide the frozen sample in a magnetic field. In one such embodiment, the sample is melted prior to detection and the freezing, polarizing, melting and detecting steps are repeated at least once.

In certain embodiments, the analyte is a molecule (e.g., a protein) that is being studied by solid- or liquid-state NMR. In other embodiments, the analyte is an imaging agent that is being used for MRI. In such embodiments, the step of detecting is performed after at least a portion of the molten sample which comprises the polarized imaging agent has been administered to the subject being imaged. In general, the frozen sample may include any solvent; however, in certain embodiments, the frozen sample includes an amount of water, e.g., at least 50%, 60%, 70%, 80%, 90%, 95%, 99% or 100% by volume of water.

In one embodiment, the methods of the present invention do not include a step of melting the sample to produce a molten sample. According to such embodiments, the sample is frozen in the detection step and the nuclear spin transitions in the at least one spin half nucleus of the analyte in the frozen sample are detected by solid-state NMR.

In another embodiment, the methods of the present invention do include a step of melting the sample to produce a molten sample. According to such embodiments, the sample is molten in the detection step and the nuclear spin transitions in the at least one spin half nucleus of the analyte in the molten sample may be detected by liquid-state NMR. Alternatively, the nuclear spin transitions in the at least one spin half nucleus of the analyte in the molten sample may be detected by MRI. According to this last embodiment, at least a portion of the molten sample that includes polarized analyte is administered (e.g., by injection, ingestion, inhalation, etc.) to a subject prior to detection. In certain embodiments (e.g., when the radical is toxic) the polarized analyte may be separated from the radical prior to administration. U.S. Pat. No. 6,311,086, the contents of which are incorporated herein by reference, describes several methods for achieving such a separation (e.g., physical and chemical separation or extraction techniques).

In general, the methods may be used to polarize any analyte. Without limitation, the analyte may be a protein or nucleic acid. Numerous solid-state and liquid-state NMR methods have been developed to study the structures of these biomolecules, e.g., one dimensional techniques, multi-dimensional techniques, including without limitation techniques that rely on NOESY, ROESY, TOCSY, HSQC, HMQC, etc. type polarization transfers and combinations thereof. Any of these techniques and variants thereof may benefit from the enhanced NMR signals that can be provided by the inventive methods. The inventive methods may also be advantageously used to improve the detection of analytes (e.g., metabolites) that are present in a sample at low concentrations (e.g., less than 1 μM, less than 100 nM, less than 10 nM or even less than 1 nM). When the analyte is being used as an imaging agent for an MRI experiment then it will preferably include at least one spin half nucleus with a long $T_1$ relaxation time. This will ensure that the enhancement is not lost by relaxation in between the polarizing and detecting steps. For example, U.S. Pat. No. 6,311,086 describes imaging agents that include spin half nuclei with $T_1$ relaxation times of at least 6 seconds at 310 K in $D_2O$ in a magnetic field of 7 T. It will be appreciated that any of the imaging agents that are described in U.S. Pat. No. 6,311,086 may be used as an analyte in an inventive method. It is also to be understood that any known MRI technique may be used to image the spatial distribution of a polarized analyte once administered to a subject (e.g., see MRI in Practice Ed. by Westerbrook et al., Blackwell Publishing, Oxford, UK, 2005, the contents of which are incorporated herein by reference).

Any spin half nucleus within the analyte may be polarized according to the inventive methods. In one embodiment, the spin half nucleus is a $^1$H nucleus. In one embodiment, the spin half nucleus is a $^{13}$C nucleus. In one embodiment, the spin half nucleus is a $^{15}$N nucleus. In one embodiment, the spin half nucleus is a $^{19}$F nucleus. The spin half nucleus may be present in the analyte at natural abundance levels. Alternatively, stronger signals may be obtained if the spin half nucleus (e.g., $^{13}$C, $^{15}$N, $^{19}$F, etc.) is enriched at one or more positions within the analyte. A variety of methods are known in the art for enriching one or more sites of an analyte (e.g., a protein, nucleic acid, metabolite, imaging agent, etc.). When the at least one spin half nucleus has a γ-value smaller than that of $^1$H (e.g., $^{13}$C, $^{15}$N, $^{19}$F, etc.) then in certain embodiments, the step of polarizing may further involve irradiating the frozen sample with radiation having a frequency that causes cross-polarization between a $^1$H nucleus present in the sample (e.g., without limitation from $^1$H$_2$O) and the at least one spin half nucleus of the analyte.

The inventive methods may be performed under any magnetic field strength. In one embodiment the field may have a strength in the range of about 0.1 T to about 30 T. For example, some of the experiments that are described herein were performed at 5 T. The radiation for exciting electron spin transitions in the unpaired electron(s) of the polarizing agent at these fields will be in the range of about 2.8 GHz to about 840 GHz. For examples, the radiation in the experiments that are described herein was from a 140 GHz gyrotron.

When studying molten samples (e.g., by liquid-state NMR), the sample may be recycled by freezing the sample, repolarizing the at least one spin half nucleus of the analyte by irradiating the frozen sample with radiation having a frequency that excites electron spin transitions in the compound, remelting the frozen sample to produce a molten sample, and redetecting nuclear spin transitions in the at least one spin half nucleus of the analyte in the molten sample. This process can be repeated for as many cycles as needed. This can be used, e.g., to signal average NMR signals and thereby further enhance the sensitivity of the NMR experiment. The freezing step can generally be achieved by cooling the sample until it reaches a solid state. In certain embodiments, the sample can be cooled to a temperature of less than about 200 K. For example, the sample may be cooled to a temperature in the range of about 1 K to about 100 K. Some of the experiments that are described herein involved cooling the sample to a temperature of about 90 K. In one embodiment, the freezing step may be completed in less than about 2 minutes, e.g., less than about 1 minute.

In general, once a frozen sample has been polarized according to the present invention it can be optionally melted prior to signal detection using any suitable method. In certain embodiments, this is achieved by exposing the frozen sample to radiation having a wavelength of less than about 100 µm, e.g., in the range of about 0.5 µm and about 50 µm. In one embodiment, the radiation may come from a laser, e.g., a CO$_2$ laser. In another embodiment, the radiation may come from a lamp, e.g., an infra-red lamp. The frozen sample can be exposed to the radiation using an optical fiber. This will typically involve coupling the radiation (e.g., from a laser or lamp) to one end of the fiber, e.g., using a lens. In one embodiment, the sample is within a cylindrical rotor. Advantageously, the rotor can be made of quartz which allows both microwave radiation (e.g., the 140 GHz radiation from a gyrotron) and infra-red radiation (e.g., from a CO$_2$ laser) to reach the sample. In addition, a quartz rotor typically does not crack when exposed to multiple freeze-thaw cycles. Finally, the use of a cylindrical rotor enables the sample to be spun during the melting step (and optionally during other steps including the detecting step), which we have found to significantly improve melting homogeneity and time. In the experiments that are described herein we were able to melt samples in less than about 1 second.

Preparation

A variety of compounds of Structural Formula (I) can be prepared according to Scheme 1:

Scheme 1. Preparation of Intermediate

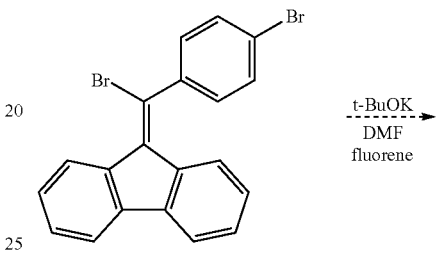

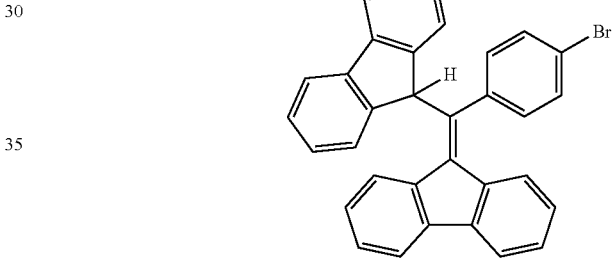

The bromo group on the phenyl moiety can readily be reacted with additional functional groups, such as fluoroalkyl groups. In one example, n-C$_8$H$_{17}$I is reacted with the intermediate above in the presence of copper and 2,2'-bipyridine in DMSO to form a perfluorinated intermediate. The perfluorinated intermediate can then be sulfonated using (1) fuming sulfuric acid and subsequent treatment with a hydroxide salt (e.g., KOH, NaOH) or (2) chlorosulfonic acid in dichloromethane to form a sulfonated anion. The sulfonated anion can be oxidized with (1) potassium butoxide and K$_3$Fe(CN)$_6$ or (2) AgNO$_3$ in dimethylformamide; tetrahydrofuran and toluene.

EXAMPLES

Example 1

Synthesis of Sulfonated BDPA

BDPA is an air stable persistent radical that shows no dimerization in solid or in solution. BDPA has an extremely narrow EPR linewidth (Δ=20 MHz at 140 GHz), and can be used for OE and SE and TM DNP NMR. While BDPA is an excellent polarization agent, its utility in biological applications is limited by lack of solubility in aqueous media.

Scheme 2. Synthesis of water soluble BDPA•

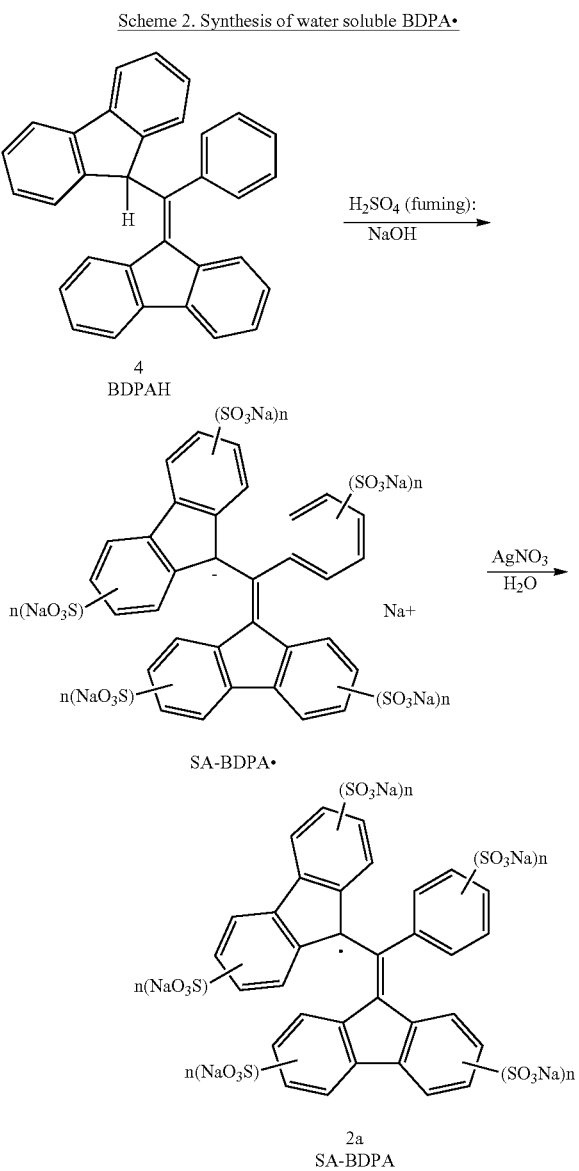

Synthesis of SA-BDPA (2a) was accomplished by treating BDPAH (4) with fuming sulfuric acid followed by deprotonation and oxidation (Scheme 2). BDPAH can be prepared in 4 steps from commercially available materials.

Specifically, 100 mg (0.239 mmol, 1 equiv) of BDPAH (4) and 1 mL fuming sulfuric acid were heated at 85° C. while stirring for 5 min. The resulting brown solution was carefully diluted with 20 mL of deionized water and the resulting salmon-colored solution stirred at room temperature for 16 h and was filtered to remove any insoluble material. The filtrate was treated with 16 mL of 10% NaOH and concentrated. The resulting deep blue powder was extracted with 125 mL of DMSO. The resulting sodium salt SA-BDPA-($\lambda_{max}$=628 nm) was precipitated from the DMSO solution with 75 mL of benzene; and washed with DCM. The dark blue powder was dissolved in 3 mL of water and 102 mg (0.598 mmol, 2.5 equiv) of $AgNO_3$ in 2 mL of water was added while stirring. The resulting red mixture stirred at room temperature for 3 h and then was filtered and concentrated to give 200 mg red powder. This was chromatographed on C18 reverse phase column eluting with 5% $H_2O$—$CH_3CN$ to give 189 mg (85%) of deep red glassy solid EPR g=2.00233 UV-Vis (water): $\lambda_{max}$=508(12000), 881 (800) nm ($\epsilon$).

Alternatively, 0.53 g (1.27 mmol, 1 equiv) of BDPAH (4) and 1 mL fuming sulfuric acid were heated at 85° C. while stirring for 6 h. The resulting black solution was carefully diluted with 10 mL of deionized water, and the pH of resulting salmon-colored solution was brought to 9 by addition of aqueous $Ba(OH)_2$. $BaSO_4$ was filtered out and the blue filtrate was treated with DOWEX HRC-W2 Na+ form. The resulting violet-blue solution was shaken with 5 g of $PbO_2$ until the color changed to deep red (30 min), and then filtered onto Amberlite IRC-50 (—COOH form). The ion exchange resin was separated, and the deep red solution was adsorbed onto RP C18 silica gel in vacuo at 50° C. This was dry loaded onto C18 reverse phase column and eluted with 200 proof ethanol followed by 20% $H_2O$-EtOH to give 400 mg (28%) of a deep red glassy solid (BDPA($SO_3Na$)$_7$). IR (ATR, Ge) 3449, 1640, 1390, 1184, 1112, and 1041 cm$^{-1}$. ESI$^-$ was obtained after ion exchange on DOWEX HRC-W2 (H+ form) MS (ESI) m/z calcd for $C_{33}H_{20}O_{21}S_7.^-$ 975.9, found 975.9. Further elution with 40% $H_2O$-EtOH yields an additional material, which consists of a mixture of sulfonation products BDPA($SO_3Na$)$_{4-7}$ Reaction time and temperature may be adjusted to increase or reduce the amount of sulfonation. The sulfonation can be carried out at r.t. over 3 days to produce completely water-soluble product mixture.

Example 2

Synthesis of Sulfonated DPPH

Reactions with sulfuric acid and chlorosulfonic acid, followed by hydrolysis of the resulting sulfonyl chloride, can be used to generate a variety of water soluble stable radicals starting from the non-water soluble precursors. Preliminary results show that DPPH can be reacted with chlorosulfonic acid to generate a water soluble radical after hydrolysis.

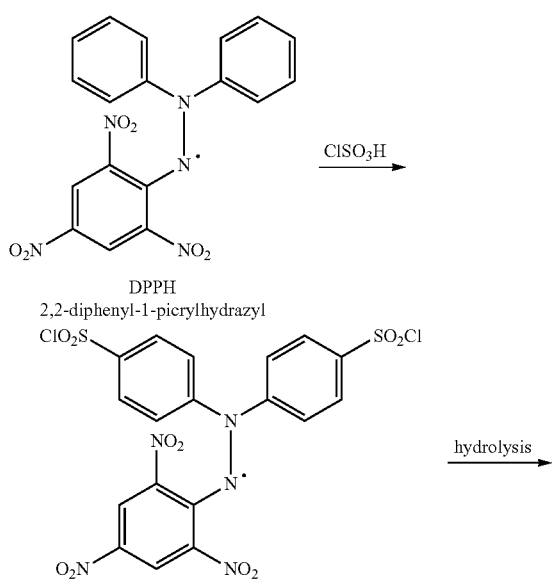

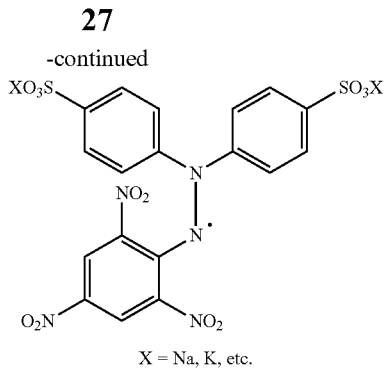

X = Na, K, etc.

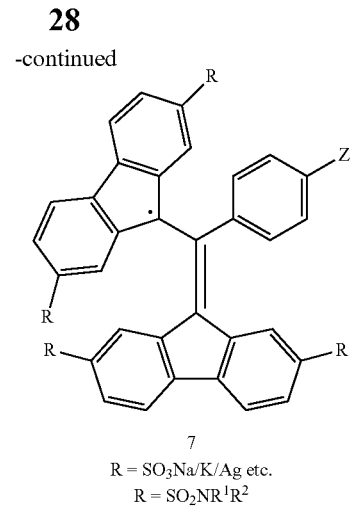

7
R = SO$_3$Na/K/Ag etc.
R = SO$_2$NR$^1$R$^2$

Example 3

Synthesis of Sulfonated/Sulfonamidated BDPA

Reaction of BDPAH derivatives (5) with chlorosulfonic acid produces chlorosulfonates (6), which can be hydrolyzed or reacted with a variety of amines prior to oxidation to give both ionic and neutral polarization agents.

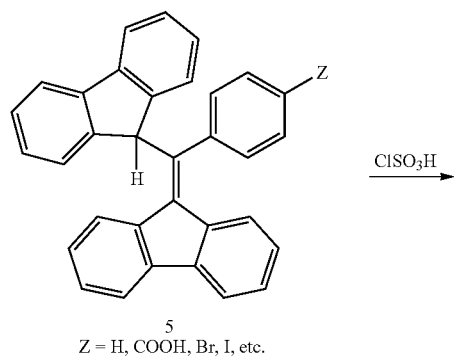

5
Z = H, COOH, Br, I, etc.

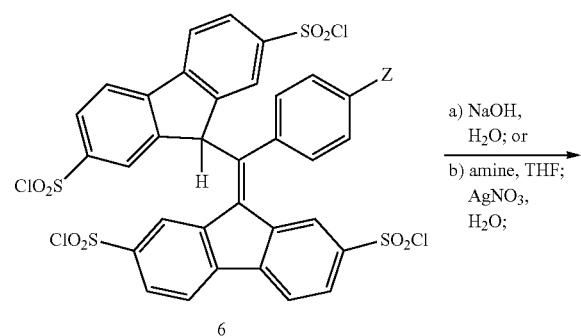

Figure 5:
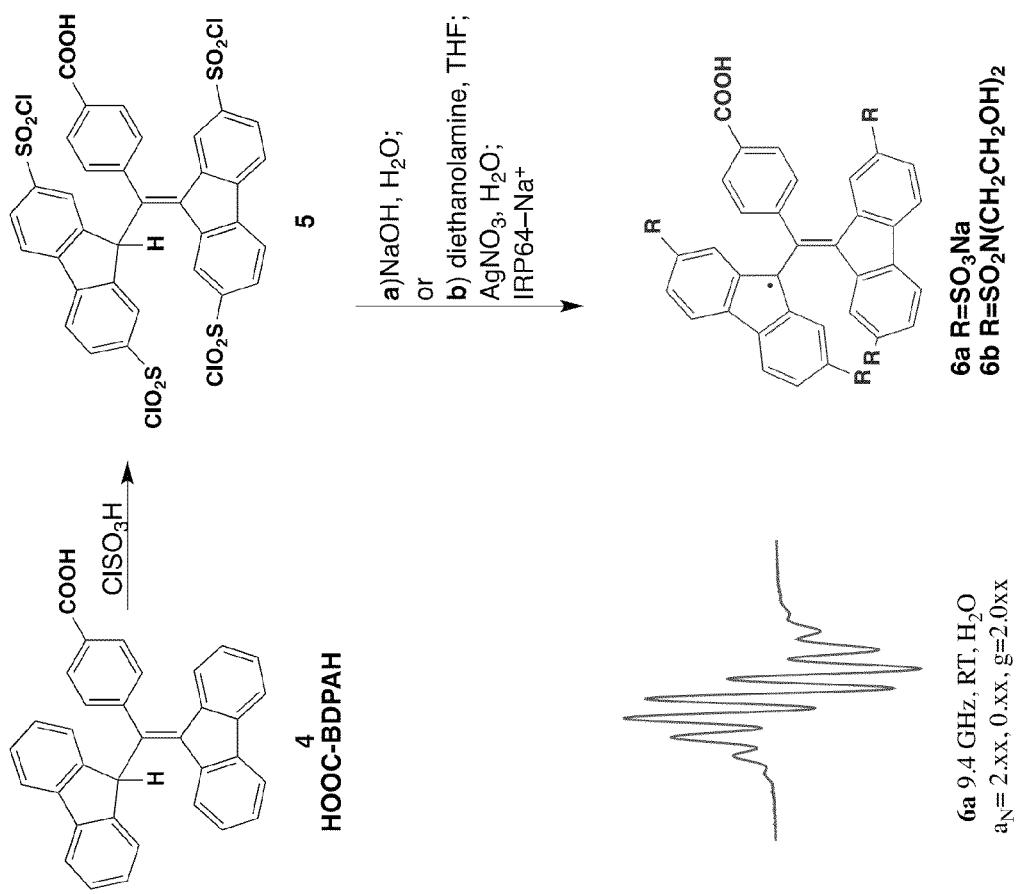
FIG. 5 shows a scheme for preparing a carboxy- and sulfonate-substituted BDPA, along with the EPR spectrum of the compound.

6

Where Z=COOH, reaction of HOOC-BDPAH (5) with chlorosulfonic acid produces chlorosulfonate 6 which can be hydrolyzed or reacted with a variety of amines prior to oxidation to give both ionic and neutral polarization agents. For example, treatment of 6 with sodium hydroxide in water followed by AgNO$_3$ oxidation and cation exchange gave 7—a highly water-soluble ionic radical similar to SA-BDPA (FIG. 5). Replacing NaOH with diethanolamine gave a neutral radical 6.

Example 4

Performance of Sulfonated BDPA

The EPR spectrum of SA-BDPA (FIG. 1) shows no evidence of aggregate formation or radical dimerization in solution or glass.

Also, SA-BDPA is air stable both in solution and as a solid. Unlike BDPA, however, SA-BDPA does not partition into organic solvents, and is soluble in water in all proportions.

Figure 2:
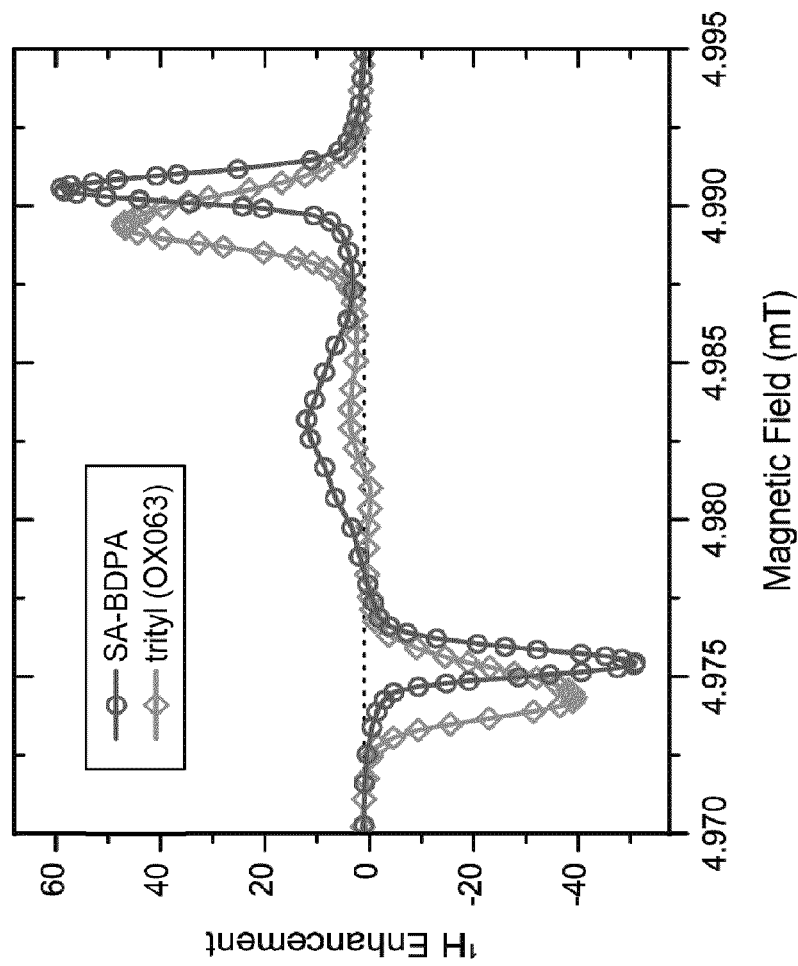
FIG. 2 shows the field-dependent $^1$H DNP enhancement of 40 mM SA-BDPA in $d_8$-glycerol/$D_2O$/$H_2O$ (60/30/10 v/v) in comparison with trityl OX063; recorded using 6 W of microwave irradiation at a frequency of 139.65 GHz under MAS conditions ($\omega_r/2\pi$=5 kHz) at ~84 K. Profiles were measured by directly detecting the $^1$H FID amplitude during Bloch decay and subsequently scaled to the enhancement value obtained after CP to $^{13}$C at the respective field position of maximum enhancement.

The field dependent DNP enhancement at 5 T (140 GHz microwave frequency) was obtained with a 40 mM frozen solution of SA-BDPA in d$_8$-glycerol/D$_2$O/H$_2$O (60/30/10 v/v) in comparison with the commonly used trityl polarizing agent OX063 (FIG. 2). $^1$H signal enhancement by DNP was observed after a Hartmann-Hahn cross-polarization step to $^{13}$C; 1 M $^{13}$C-urea was added to the solution in order to provide sufficient $^{13}$C for detection of thermal equilibrium polarization. Both radicals give the typical solid effect profile with a positive and a negative peak separated by a field corresponding to twice the Larmor frequency of the nucleus polarized and centered around the EPR resonance field. As expected, the narrower line width of SA-BDPA is retained in the DNP field profile. At the respective field of maximum enhancement SA-BDPA yields an NMR signal enhancement of $\epsilon$=61 (by comparison of on- and off-signal after 1.3×T$_B$ at 6 W microwave power), approximately 30% higher than the enhancement obtained with trityl under the same conditions.

In addition to the signals attributed to SE, another feature centered at the EPR resonance field of 4.983 mT was observed for SA-BDPA. Experiments have shown a $^1$H enhancement of approximately 8 independent of the applied microwave power in the range between 2.4 and 10 W (not shown). This flat power dependence together with the increased width of this feature indicates that it is likely that the underlying mechanism is solely based on direct saturation of the EPR resonance and nuclear polarization is induced via cross-relaxation, similar to the Overhauser effect. Cross effect or thermal mixing is unlikely to be causing this peak, because both mechanisms require much larger EPR line width and typically yield a DNP field profile with regions of positive and negative enhancements and an overall width comparable to the EPR line width. The feature in the center of the trityl profile was attributed to CE/TM. The SA-BDPA profile does not show any sign of CE/TM, which is in accordance with the significantly reduced line width of SA-BDPA compared to trityl (28 MHz vs. 50 MHz).

Previous studies of the solid effect have shown that the polarization enhancement is accompanied by a shortening of the time constant at which nuclear longitudinal polarization builds up. Therefore, a careful analysis of the build-up dynamics and extrapolation of the signal intensity at infinite polarization time is crucial in order to prevent misinterpretation of data.

Figure 3:
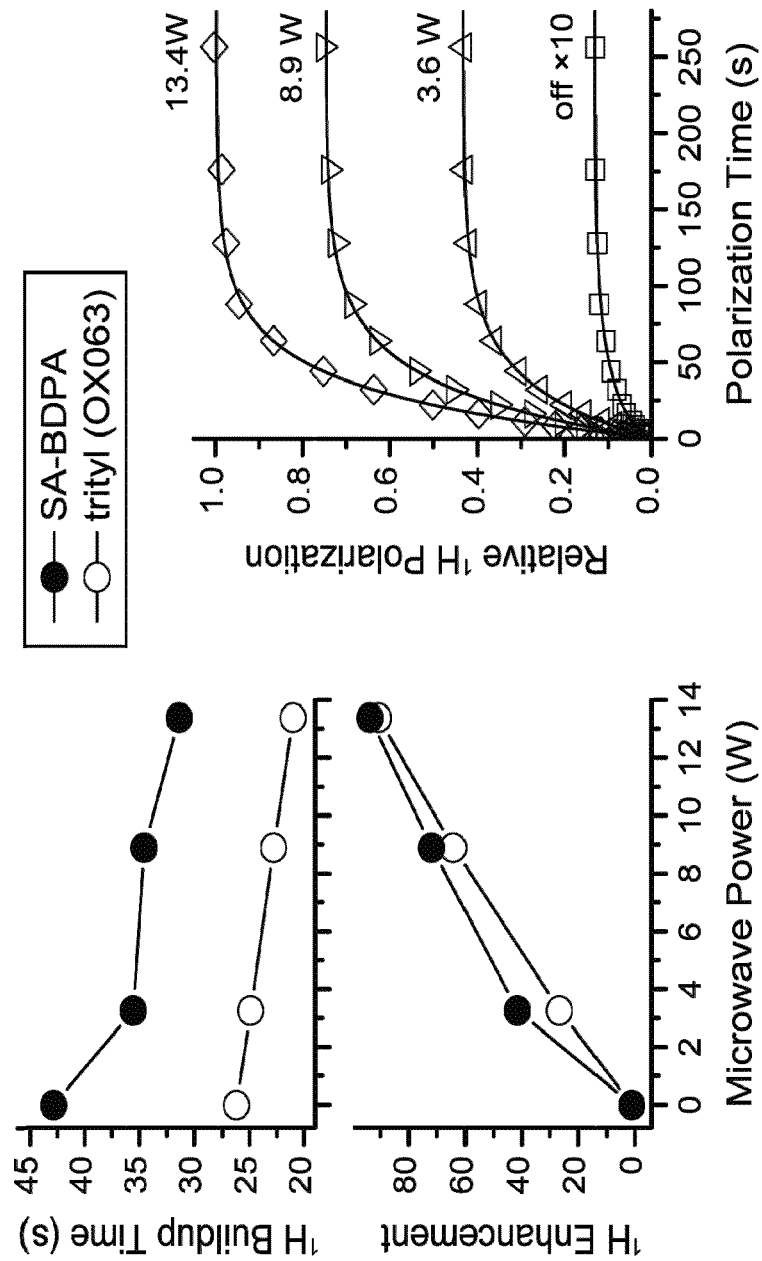
FIG. 3 shows the buildup time constant (top left) and enhancement at infinite polarization time (bottom left) obtained with 40 mM SA-BDPA in $d_8$-glycerol/$D_2O$/$H_2O$ (60/30/10 v/v). Parameters have been obtained by fitting polarization buildup curves (right) with exponential functions. All data recorded using microwave irradiation at a frequency of 139.65 GHz under MAS conditions ($\omega_r/2\pi$=5 kHz) at ~84 K. Signal intensity was measured as 13 polarization of 1 M 13C-urea after $^1$H-$^{13}$C CP step. Trityl OX063 comparison data taken from reference [xy](recorded under similar conditions).

Buildup time constants show values between 43 s and 32 s, depending on the incident microwave power and obtained enhancements; these values are approximately 50% larger in comparison with trityl under similar conditions, which is attributed to less efficient longitudinal relaxation enhancement of protons by the paramagnetic species (FIG. 3). This explanation is further supported by significantly larger spin-lattice relaxation of the respective electron spin (58.6 ms in SA-BDPA vs. 1.43 ms in OX063). This longer spin-lattice relaxation time might also lead to a "saturation effect" observed in microwave power dependent measurements of the $^1$H DNP enhancement. While trityl shows a near linear power dependence, the enhancements obtained with SA-BDPA are more than 50% larger at lowest applied power, but approach those obtained with trityl at the highest output power available.

Figure 4:
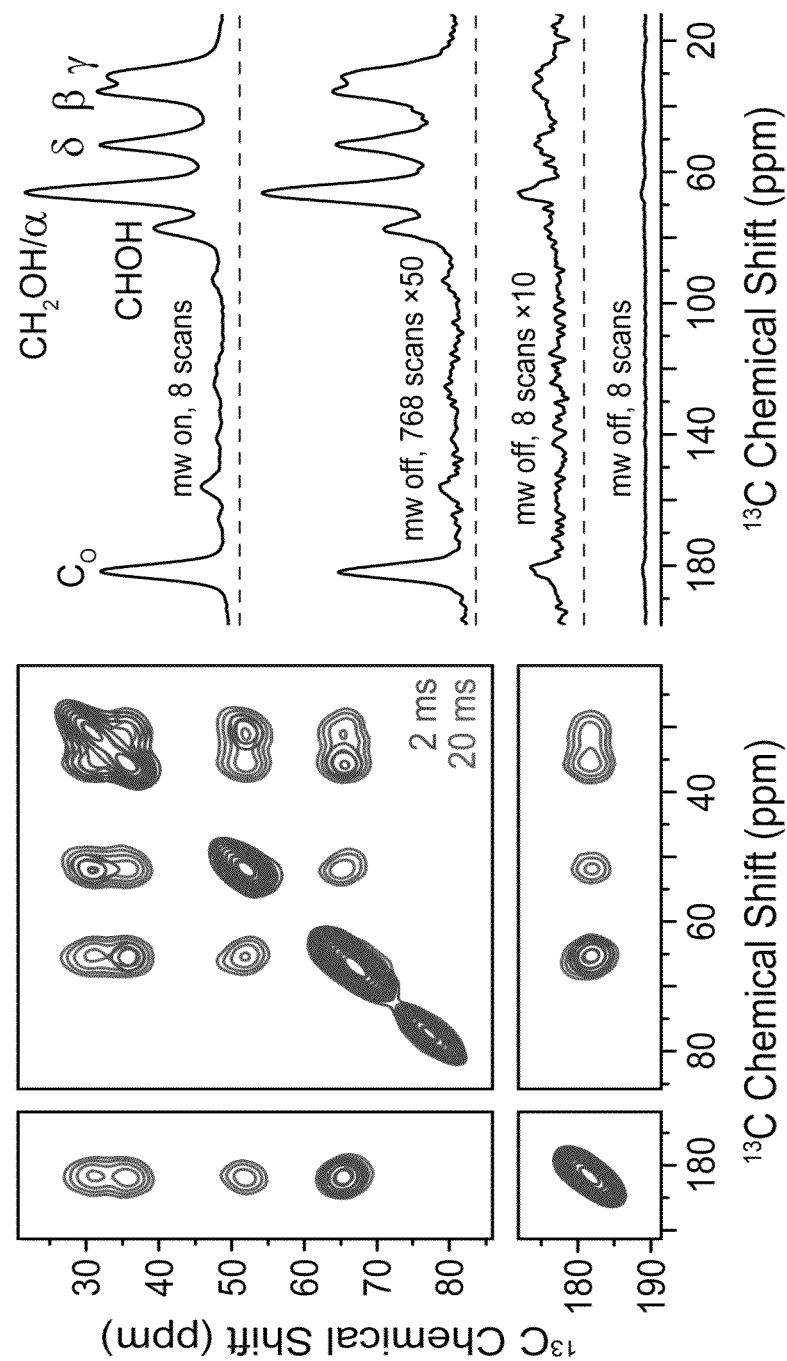
FIG. 4 shows a DNP enhanced 2D $^{13}$C-$^{13}$C correlation spectrum (spin-diffusion) using 2 ms (green) and 20 ms (red) mixing time (left) and $^{13}$C CPMAS spectra (right) of 0.1 M $^{13}C_5$-proline polarized by 40 mM SA-BDPA in $d_8$-glycerol/$D_2O$/$H_2O$ (60/30/10 v/v) under 8 W microwave irradiation at a frequency of 139.65 GHz and MAS conditions ($\omega_r/2\pi$=5 kHz) at ~84 K.

DNP enhanced 1D CPMAS and 2D correlation spectra (FIG. 4) of a 0.1 M solution of uniformly labeled proline in the same solvent mixture described above. $^{13}$C-$^{13}$C mixing was achieved using spin-diffusion assisted by a DARR field applied to $^1$H. Homonuclear mixing has been limited either to a one-bond distance (FIG. 4, green) or has been allowed to occur between all nuclei in the small molecule (FIG. 4, red) by allowing spin-diffusion for a mixing period of 2 ms or 20 ms, respectively. In both cases, all expected cross-peaks are present and clearly resolved. $^1$H signal enhancement was determined as ϵ=50 by comparison of signal amplitudes with and without microwave irradiation (see FIG. 4, right).

Equivalents

The section headings used herein are for organizational purposes only and are not to be construed as limiting the subject matter described in any way.

While the present invention has been described in conjunction with various embodiments and examples, it is not intended that the present invention be limited to such embodiments or examples. On the contrary, the present invention encompasses various alternatives, modifications, and equivalents, as will be appreciated by those of skill in the art.

While the present invention has been particularly shown and described with reference to specific illustrative embodiments, it should be understood that various changes in form and detail may be made without departing from the spirit and scope of the present invention. Therefore, all embodiments that come within the scope and spirit of the present invention, and equivalents thereto, are intended to be claimed.

What is claimed is:
1. A compound represented by structural Formula (I):

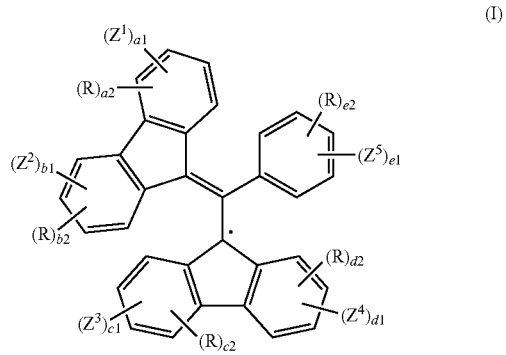

wherein:
each R is independently —R', —OR', —SR', halogen, —CN, —NO2, —NR'R", polyethyleneglycol —COOR', —OCOR', —CONR'R", or —NR'COR", or

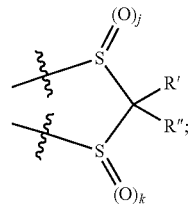

two R on adjacent carbon atoms taken together are
Z$^1$-Z$^5$ are each independently —SO$_2$X, —SO$_3$X or —SO$_2$NR'R";
R' and R" are independently —H, an optionally substituted alkyl or an optionally substituted aryl;
X is a cation;
a1, b1, c1 and d1 are each integers from 0 to 4, wherein the sum of a1, b1, c1 and d1 is one or greater;
a2, b2, c2 and d2 are each independently integers from 0 to 4;
e1 and e2 are each independently an integer from 0 to 5; and
j and k are independently integers from 0 to 2.

2. The compound of claim 1, wherein Z$^1$-Z$^5$ are each independently —SO$_3$X.

3. The compound of claim 2, wherein X includes H$^+$, NR'R"R"'R"", Ag$^+$, Ca$^{2+}$, Ba$^{2+}$, Li$^+$, Na$^+$ or K$^+$ or a combination thereof and wherein R', R"R"' and R"" are each independently —H, an optionally substituted alkyl or an optionally substituted aryl.

4. A pharmaceutical composition comprising a compound of claim 3 and a pharmaceutically acceptable carrier.

5. The compound of claim 1, wherein the compound is represented by Structural Formula (Ia):

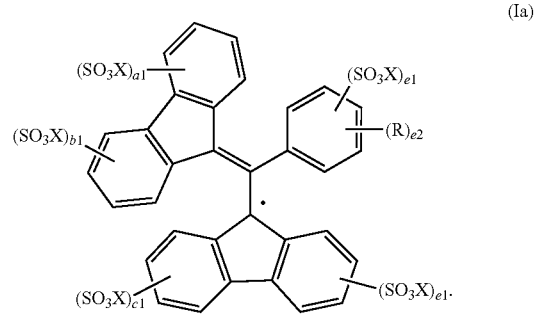

6. A pharmaceutical composition comprising a compound of claim 2 and a pharmaceutically acceptable carrier.

7. A method comprising polarizing an unpaired electron spin in a compound of claim 3.

8. A method comprising polarizing an unpaired electron spin in a compound of claim 5.

9. The compound of claim 5, wherein e1 is 1.

10. A pharmaceutical composition comprising a compound of claim 9 and a pharmaceutically acceptable carrier.

11. A method comprising polarizing an unpaired electron spin in a compound of claim 9.

12. The compound of claim 5, wherein e1 is 0.

13. A pharmaceutical composition comprising a compound of claim 12 and a pharmaceutically acceptable carrier.

14. A method comprising polarizing an unpaired electron spin in a Compound of claim 12.

15. The compound of claim 5, wherein R is —COOR', a halogen or a fluoroalkyl.

16. A pharmaceutical composition comprising a compound of claim 15 and a pharmaceutically acceptable carrier.

17. A method comprising polarizing an unpaired electron spin in a compound of claim 15.

18. The compound of claim 5, wherein the sum of a1, b1, c1, d1 and e1 is from 2 to 7.

19. The compound of claim 18, wherein the compound is:

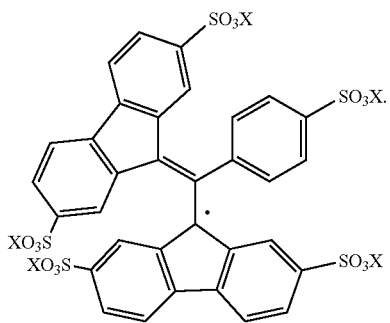

20. A pharmaceutical composition comprising a compound of claim 19 and a pharmaceutically acceptable carrier.

21. A method comprising polarizing an unpaired electron spin in a compound of claim 19.

22. A pharmaceutical composition comprising a compound of claim 18 and a pharmaceutically acceptable carrier.

23. A method comprising polarizing an unpaired electron spin in a compound of claim 18.

24. A pharmaceutical composition comprising a compound of claim 5 and a pharmaceutically acceptable carrier.

25. A method comprising polarizing an unpaired electron spin in a compound of claim 2.

26. A pharmaceutical composition comprising a compound of claim 1 and a pharmaceutically acceptable carrier.

27. A method comprising polarizing an unpaired electron spin in a compound of claim 1.

28. The method of claim 27 further comprising administering the compound to a subject for magnetic resonance imaging.

29. The method of claim 28, wherein the subject is a human.

30. A composition comprising a compound of claim 1.

31. The composition of claim 30, further comprising a stable radical.

32. The composition of claim 31, wherein the stable radical is a verdazyl, hydrazyl, nitroxide or trityl radical.

* * * * *